United States Patent [19]

Eichoefer

[11] Patent Number: 5,118,506
[45] Date of Patent: * Jun. 2, 1992

[54] PINE OIL FIRE ANT INSECTICIDE FORMULATIONS

[75] Inventor: Gerald W. Eichoefer, Liberty, Mo.

[73] Assignees: Peter F. Casella, Lewiston, N.Y.; a percentage interest; Kenneth A. McGaw, Houston, Tex.; a percentage interest

[*] Notice: The portion of the term of this patent subsequent to Jan. 2, 2007 has been disclaimed.

[21] Appl. No.: 445,372

[22] Filed: Dec. 4, 1989

Related U.S. Application Data

[63] Continuation-in-part of Ser. No. 017,739, Feb. 24, 1987, Pat. No. 891,222.

[51] Int. Cl.⁵ .................................. A01N 65/00
[52] U.S. Cl. ..................... 424/196.1; 424/DIG. 10
[58] Field of Search ................... 424/196.1, 195.1

[56] References Cited

U.S. PATENT DOCUMENTS

| | | | |
|---|---|---|---|
| 3,006,809 | 10/1961 | Gershon | 514/755 |
| 3,220,921 | 11/1965 | Greenbaum | 514/755 |
| 4,353,907 | 10/1982 | Lovell | 514/755 |
| 4,891,222 | 1/1990 | Eichhoefer | 424/196.1 |

FOREIGN PATENT DOCUMENTS

| | | | |
|---|---|---|---|
| 550878 | 11/1956 | Italy | 424/196.1 |
| 550878 | 11/1956 | Italy | 424/196.1 |
| 0908296 | 5/1980 | U.S.S.R. | 424/196.1 |
| 1464716 | 2/1977 | United Kingdom | 424/196.1 |
| 1464716 | 2/1977 | United Kingdom | 424/196.1 |

OTHER PUBLICATIONS

Perti Agarwal; Pesticides, Jul. 1969; pp. 45–47 (see AR filed Dec. 7, 1990 for abstract CA72:2084s 1970).
Bajpai, Svivastava, Perti S Agarwal, Labder J. Sci. Tech. vol. 913 No. 1, Jan. 1971; pp. 68–70, (see AS filed Dec. 7, 1990 for abstract CA76:55225b 1972).
Chem. Abst. 72:20843s (1970).
Chem. Abst. 76:55225b (1972).
Condensed Chem. Dictionary, 7th Ed. pp. 748–749.
Condensed Chem. Dictionary 9th Ed. p. 687 (1977).
Condensed Chem. Dictionary 10th Ed. p. 818 (1981).
Handbook of Chem. Synonyms & Trade Names p. 562 (1978).
Kirk-Othmer Encyclopedia of Chem Tech vol. 16 pp. 326–327 (1981).
McGraw-Hill Dictionary of Scientific & Tech Terms 4th Ed. p. 1432 (1989).

*Primary Examiner*—John W. Rollins
*Assistant Examiner*—Ralph Gitomer
*Attorney, Agent, or Firm*—Peter F. Casella

[57] ABSTRACT

This invention relates to the use of insecticidal formulations which are mixtures of pine oil and baits, especially in solid or fluid form, including paste, liquid, syrup, gaseous or mist form, and mixtures or suspensions thereof, for controlling the population of certain colonial insects, especially fire ants.

18 Claims, No Drawings ically available aluminum phosphide, sold as degesch pellets, however, has proved to be unsatisfactory because of the danger in its use by releasing toxic phosphine gas which is highly toxic to animal life as well as to insects. Amdro, a product of American Cyanamid Company, which contains fluoroaminido hydrazones, is an acceptable and effective product but is very expensive in use. Other compositions including diazonon have been used by commercial pesticide applicators with some success, however, the cost is high because of the cost of the materials as well as the cost of their application.

PINE OIL FIRE ANT INSECTICIDE FORMULATIONS

BACKGROUND OF THE INVENTION

This application is a continuation-in-part of my copending application Ser. No. 017,739 filed Feb. 24, 1987, issued as U.S. Pat. No. 4,891,222.

There is a scourge of insects invading the United States and many other parts of the world in increasing numbers, ever since government restrictions have been placed on the use of chemicals that have been employed in controlling them. The government restrictions have been imposed in the effort to protect the environment from real or imaginary toxic effects of the chemicals employed. Among the chemicals banned or restricted in use by governments are DDT, Chlorodane, Lindane, Aldrin, Heptechlor, Dieldrin and Mirex. Mirex was employed as an effective insecticide against fire ants, however, since its use has been banned in the United States, the fire ant population has been increasing so rapidly that major destruction of crops such as soybeans, potatoes, and other vegetables, has been occurring in the sun belt region of the United States where the fire ant is taking over. In addition fire ants have been known to kill young birds and even small rodents and they will feed on any thing or anybody that collapses from their multiple stings. They are a menace to people in homes, schools, work places, and even in medical facilities, to domestic animals, and especially in agriculture. Fire ants destroy lawns and forage tunnels in the ground and infest any buildings above them. One species, solenopsis invicta is reported to nest in super colonies called insect megalopolises, containing 10 to 20 million ants.

PRIOR ART

The order Hymenoptera, family Formicidae includes numerous species of ants. The order Isooptera, family Termitidae includes various species of termites. Representative species of ants and termites are given in Columns 3 and 4 in U.S. Pat. No. 4,421,759 issued to R. J. Boisvenue on Dec. 20, 1983 and assigned to Eli Lilly & Company. This patent discloses and claims the use of fluoro-benzimidazoles and fluoro-benzimidazolines for controlling ants and termites, especially fire ants.

Another patent directed to the control of fire ants is U.S. Pat. No. 4,353,907 issued to J. B. Lovell on Oct. 12, 1982 and assigned to American Cyanamid Company. This patent discloses and claims the use of fluoroaminido hydrazones and their bait formulations with edibile oils, such as soybean oil, cottenseed oil, coconut oil, corn oil, olive oil, peanut oil, palm oil, tall oil, and their mixtures, for controlling fire ants.

Still another patent directed to the control of fire ants is U.S. Pat. No. 3,220,921 issued to Greenbaum and Weil on Nov. 30, 1965 and assigned to the Hooker Chemical Corporation. This patent disclosed and claims the dimer of hexachlorocycyopentadiene, also known as Mirex, with baits such as peanut butter. Mirex was found to be one of the most effective fire ant killers and was employed in solid baits such as peanut butter and ground up corn cobs because of its pronounced toxicity when ingested in the insects digestive tract, as distinguished from its contact insecticidal activity which is not so great. Although Mirex is an effective agent for killing fire ants it can not be employed in those juristrictions where it has been banned because it is toxic to the environment.

Pine oil is a naturally occurring material, which is obtained by the distillation of the cones, needles, stumps, etc. of various species of pines, which are coniferous trees. They consist principally of isomeric tertiary and cyclic terpene hydrocarbons and alcohols, with variable quantities of terpene ethers, ketones, phenols, phenolic ethers among other constitutents, including alpha-pinene.

Various patents have been issued on the use of materials originating from pine trees. For example, U.S. Pat. No. 141,512 issued to J. B. Lunbeck back in Aug. 5, 1873 discloses a composition produced by boiling one gallon of pine tar; one quart of soft soap; one-half pint of tobacco juice and one-half gallon of alkali for use in destroying insects, worms and grubs and protecting fruit and other trees. Another patent issued to G. C. Richards on Apr. 13, 1926 discloses and claims an insecticide paint made from pine tar, a thinner, sulfur and carbolic acid. Still another patent 2,258,390 issued to W. D. Martin issued on Oct. 7, 1942 discloses the use of pine rosin in special formulations including kerosene for use as a larvacide.

In addition to the foregoing prior art, the following references were cited in my copending application Ser. No. 017,739 filed on Feb. 24, 1987 of which this application is a continuation-in-part. Chemical Abstracts 72:30843s and 76:55252b which disclose the use of synthetic pine oil with insecticides such as DDT, oils of Acorus/Curcuma and insect repellants DMP for controll of house flies, mosquitoes and leeches. British Patent 1,464,716 to Peacock et al which discloses a pine oil composition comprising an emulsifier. Russian Patent 908 296 which discloses an insect repellant comprising pine oil composition in an aqueous emulsion. Italian Patent 550.898 which discloses an insect repellant comprising pine oil, water, an emulsifier and alcohol.

OBJECTS OF THE INVENTION

It is an object of this invention to provide a composition and method which is economical, easy and safe to use, and which is effective in killing and controlling fire ants, and which is assimilable in the environment without any deleterious effects.

It is a further object of this invention to employ materials that have been present in the environment for long periods of time without any adverse effects whereby their safety and acceptability to man and his environment is already established, thereby reducing or eliminating the need for long and expensive testing and documentation in order to obtain government approval to employ the compositions and methods in commerce. These and other objects of the invention will become apparent by the disclosures made herein.

It is still a further object of this invention to provide compositions and methods for use of pine oil with baits that attract fire ants, which compositions are preferrably in solid or fluid form including paste form, but which may be in liquid, syrup, gaseous or mist form, and mixtures or suspensions thereof, and which act as poisons in the food chain to kill the fire ants by injestion and/or by respiratory contact; while at the same time being relatively non-toxic to human and animal life forms, as well as being assimilable in the environment without deleterious effect.

BRIEF DESCRIPTION OF THE INVENTION

These objects are accomplished by applicant's invention comprising mixtures of pine oil and baits in solid or fluid form, including paste, liquid, syrup, gaseous or mist form, and mixtures or suspensions thereof, that kill fire ants when the mixture is injested or contacted, including respiratory contact by fire ants, as more fully described and claimed.

DETAILED DESCRIPTION OF THE INVENTION

In order that this invention may be more readily understood it will be described with respect to certain preferred embodiments, however it is to be understood that these embodiments are not to be construed as limiting the invention except as defined in the appended claims.

The preferred compositions of this invention are prepared by making a mixture of an insecticidal amount of pine oil with a bait. More preferably, the compositions are between about one part of pine oil to one hundred parts of a bait and about 99 pine oil to 1 of bait, to form a solid or fluid form, including paste, liquid, syrup, gaseous or mist form, and mixtures or suspensions thereof, of the ingredients. Smaller amounts of pine oil, such as 0.1 parts per 100 parts of bait may be employed. The composition is used in the field by broadcasting it as pellets or chuncks or by spreading or pouring the pastes or syrups or spraying the gaseous or mist forms in the vacinity of the fire ant mounds. The compositions may be applied without a container, or if preferred may be distributed in perforated containers of paper, plastic, metal and the like.

Table 1 gives the results obtained in testing over 60 fire ant mounds. Ten of the mounds were used as controls, five of which had nothing done to them and five of which had plain water, in like amounts to the compositions of this invention being tested, poured over them. In Table 1 the "Date" is given in months/day; the "Location" were all in the southern part of Texas; the "Condition" is the weather condition at the time of the test; "Time" is given in 24 hour clock terms; the "Temp" is in Fahrenheit; "Product" is the material actually employed in the test; complete descriptions of the Products tested are given in the footnotes to the Table; "Mound Size" is measured in inches and the "Results" are given in percentage of kill of the fire ants, with the time required to get the percentage kill.

Table 2 gives the details on the commercial products available for controlling and killing fire ants.

Table 3 gives the composition ranges for individual components found in United States Domestic pine oils, which may be employed in accordance with this invention.

My copending application Ser. No. 017,739 discloses and claims methods and compositions for controlling fire ants by applying a composition to the locus containing the fire ants comprising pine oil, an emulsifying amount of a surfactant and water. Said compositions are employed by various techniques, such as by contacting the mounds of fire ants with the solutions by drenching, pouring, injecting into or spraying the mounds.

In both Ser. No. 017,739, and this application, Table 1, page 6 thereof, in paragraph 11, discloses that my pine oil compositions also kill fire ants by entering their food chain, presumably by injestion, and may be employed in solid or paste form with baits. Unipine 85, is disclosed which is a pine oil containing 87.8% terpene alchols, 11.9% terpene hydrocarbons and 0.3% water meeting U.S. Government specification LLL-P-400A Type 1, with peanut butter as the bait, which is effective in causing a substantial kill of fire ants, in a relatively short time frame.

Table 4 A shows examples in solid or fluid form, and Table 4 B shows the insecticidal results obtained when employing them in the food chain of fire ants or by respiratory contact.

The baits were made by mixing the ingredients together until a fairly uniform composition was obtained. Table 4 A shows the characteristics of the insecticidal baits. The data given in Table 4 B was obtained by placing 100 fire ants, from mounds in the Houston, Tex., area, and about one-half ounce of the bait, into a ventilated two quart jar. Periodic readings of the number of fire ants killed against time are given in Table 4 B. Controls without pine oil showed no kill.

TABLE 1

| \multicolumn{8}{c}{TEST MONITORING LOG} |
|---|---|---|---|---|---|---|---|
| Date | Location | Condition | Time | Temp | Product | Mound Size | Results |
| 9/16 | Woodbranch Field | Hot/ Clear | 14:30 | 90 | Raid | 12 × 5 | 75% kill 30 minutes 95% kill 1 hour |
| 9/16 | Woodbranch Field | Hot/ Clear | 14:30 | 90 | Prod Five | 10 × 4 | 75% kill 20 minutes 95% kill 1 hour |
| 10/26 | Residential Lawn | Cloudy | 15:30 | 71 | Prod Five | 12 × 4 | 60% kill 20 minutes 100% kill 22 hours increased solution to ¼ C |
| 10/26 | Residential Lawn | Cloudy | 15:30 | 71 | Enforcer | multiple | negligible 20 minutes negligible 22 hours |
| 10/26 | Residential Lawn | Cloudy | 15:30 | 71 | Raid | 9 × 4 | 75% kill 20 minutes 90% kill 22 hours |
| 10/26 | Residential Lawn | Cloudy | 15:30 | 71 | Prod Five | 10 × 3 | 75% kill 20 minutes 95% kill 2½ hours 100% kill 22 hours |
| 10/26 | Residential Lawn | Cloudy | 15:30 | 71 | Enforcer | 2' × 5" | No impact 2 hours Mound abandoned 3 days |
| 10/28 | Residential Lawn | Cool/ Rainy | 10:30 | 65 | Raid | 9 × 3 | 90% kill 30 minutes |
| 10/28 | Residential Lawn | Cool/ Rainy | 10:30 | 65 | Prod Five | 9 × 3 | 100% kill 30 minutes |
| 10/28 | Residential Lawn | Cool/ Rainy | 10:30 | 65 | Amdro | 10 × 4 | No impact 2 hours Mound abandoned 2 days |
| 10/28 | Residential Lawn | Cool/ Rainy | 10:30 | 65 | Rid-A-Bug | 12 × 4 | 75% kill 2 hours |
| 4/24 | Woodbranch | P Cldy | 11:50 | 78 | P5/UD | 18 × 5 | 80% kill 20 minutes |

TABLE 1-continued

TEST MONITORING LOG

| Date | Location | Weather | Time | Temp | Product | Size | Result |
|---|---|---|---|---|---|---|---|
| | Field | | | | | | 100% kill 35 minutes |
| 4/24 | Woodbranch Field | P Cldy | 11:55 | 78 | P5/UP | 12 × 6 | 100% kill 20 minutes |
| 4/24 | Woodbranch Field | P Cldy | 12:00 | 78 | P5/AT | 14 × 5 | 10% kill 20 minutes<br>20% kill 40 minutes |
| 4/24 | Woodbranch Field | P Cldy | 12:08 | 78 | Raid | 10 × 7 | 15% kill 20 minutes<br>60% kill 40 minutes |
| 4/24 | Woodbranch | P Cldy | 12:15 | 78 | P5/UP | 10 × 9 | 100% kill 15 minutes |
| 4/26 | Residential B. Hill | Clear | 17:15 | 72 | P5/UP | 12 × 12 | 100% kill 15 minutes kills grass |
| 4/26 | Residential B. Hill | Clear | 17:15 | 72 | P5/UP | 10 × 10 | 100% kill 18 minutes kills grass |
| 4/26 | Residential M. Craven | Clear | 9:15 | 72 | P5/UP | 20 × 2 | 100% kill 10 minutes browns grass |
| 4/26 | Residential M. Craven | Clear | 9:25 | 72 | P5/UP | 8 × 8 × 8 | 100% kill 15 minutes |
| 4/26 | Residential M. Craven | Clear | 17:30 | 74 | P5/AT | 15 × 9 | 25% kill 20 minutes<br>30% kill 40 minutes |
| 4/26 | Residential D. Hennley | Clear | 16:15 | 73 | P5/UP | 16 × 20 | 90% kill 10 minutes kills grass |
| 4/26 | Residential D. Hennley | Clear | 16:20 | 73 | P5/UD | 15 × 16 | 80% kill 20 minutes |
| 10/4 | Residential W. Sublette | Cloudy | 14:40 | 70 | P5/PB/UP | 12 × 6 | 20% slow kill on surface 2 day duration |
| 10/4 | Residential W. Sublette | Cloudy | 14:50 | 70 | Peanut Butter only | 10 × 6 | Negligible kill |
| 10/4 | Residential W. Sublette | Cloudy | 15:05 | 70 | Surfactant & Water | 14 × 4 | None |
| 10/5 | Residential D. Hennley | Cloudy/Rain | 14:30 | 71 | P5/PB/UP | 14 × 5 | 25% slow kill on surface |
| 10/5 | Residential D. Hennley | Cloudy/Rain | 14:40 | 71 | Peanut Butter only | 10 × 3 | Negligible kill |
| 10/5 | Residential D. Hennley | Cloudy/Rain | 14:45 | 71 | Surfactant only | 12 × 3 | None, browns grass |
| 10/5 | April Vlg cul-de-sac | Cloudy/Rain | 15:05 | 71 | Water only | 9 × 2 | None |
| 10/5 | April Vlg cul-de-sac | Cloudy/Rain | 15:10 | 71 | UP & Water | 11 × 3 | 80% kill in 20 minutes spotty kill pattern due to poor suspension |

NOTES

1. Product 5 as indicated on Page 1 of Table 1 was the initial mixture used to test the hypothesis and consisted of ½ cup Real-Pine (a commercially available disinfectant with a composition of 30% pine oil) and ½ cup surfactant (Dawn Dishwashing Detergent) mixed in 1 gallon of water. The solution was mixed and poured on the villages as a mound drench. Ingredients are as follows:

| | | |
   |---|---|---|
   | Real-Pine: | Pine Oil | 30% |
   | | Soap | 11% |
   | | Isopropanol | 9% |
   | | Inert Ingredients | 50% |
   | Dawn: | Water | 50% |
   | | Magnesium Alkyl Sulfate | 15% |
   | | Magnesium Alkyl Ethoxylate Sulfate | 15% |
   | | Amoniam Alkyl Ethoxylate Sulfate | 7% |
   | | Ethenyl | 7% |
   | | Amin Oxide | 2% |
   | | Amonium Chloride | 2% |
   | | Amonium Zyline Sulfinate | 2% |
   | | Trace of Minor Ingredients | |

2. Raid as indicated on Page 1 of Table 1 is a commercially available consumer product which is a concentrated mound drench solution that must be added to water. Ingredients by label are:

| | | |
   |---|---|---|
   | Active Ing: | Chlorpyrifos [0,0-Diethyl-0-(3,5,6-trichlor-2-pyridyl)phosphorothioate | 2.00% |
   | Inert Ingredients: | | 98.00% |

3. Enforcer is a commercially available consumer product in an aerosol form utilizing an injection tube to penetrate the mound. Its ingredients by label are:

| | | |
   |---|---|---|
   | Active Ing: | Tetramethrin [1-Cyclohexene-1, 2-Dicarboximido)methyl 2. 2-Dimethyl-3-(2-methylpropenyl) Cylopropanecarboxlate] | 0.200% |
   | | Cyano (3-Phenoxyphenyl) Methyl 4 chloro-alpha-(1-methylethyl) Benezeneacetate | 0.400% |
   | | Petroleum Distillate | 2.278% |
   | Inert Ingredients: | | 97.122% |

4. Amdro is a commercially available consumer product which is a solid bait. It is sprinkled on the mound in significant proportion to cover the mound area. Ingredients by label are:

| | | |
   |---|---|---|
   | Active Ing: | Tetahydro-5, 5-dimethyl-2 (1$\underline{H}$)-phrinidinone (3-4[trifluoromethyl) phenyl]-1-(2-[4-(trifluoromethyl) phenyl]-ethenyl)-2-propenylidene | 0.88% |
   | Inert Ingredients: | | 99.12% |

5. Rid-A-Bug is also a commercial mound drench solution. Its ingredients by label are:

| | | |
   |---|---|---|
   | Active Ing: | Chlorpyrifos [(0,0-diethyl 0-(3,5,6-trichloro-2-pyridyl) phosphorothioate | 0.50% |
   | | 3,7-Dimethyl-6-octen-1-ol | 0.011% |
   | | 3,7-Dimethyl-2-6-octedien-1-ol | 0.002% |

TABLE 1-continued
TEST MONITORING LOG

|   |   |   |
|---|---|---|
|   | 3,7-Dimethyl-6-octanol | 0.002% |
|   | Xylene lange aromatic solvent | 0.28% |
| Inert Ingredients: |   | 99.205% |

6. All commercial products were applied by following label directions at the same time applications of my product were made to other mounds in the exact same conditions.
7. After further testing components in Real-Pine, it was determined that pine oil was the active ingredient. Further experiments were carried out with chemically produced versions of natural pine oil.
The "product" codes shown on Page 2 substitute the ⅛ cup Real-Pine for ⅛ cup measures of three other substances. P5/UD indicates Unitene DTR was substituted for Real-Pine. P5/UP is the designation for Unipine 85 substituted for Real-Pine, while P5/AT indicates Alpha Terpineol was the substitute. In all cases the substitute was exactly ⅛ cup of the chemical to ⅛ cup surfactant and ⅛ cup N-Butyl Acetate. While the substitutes showed varying degrees of results, the inclusion of N-Butyl Acetate neither enhanced or negated the kill ratio and was only for masking agent purposes.
8. The results utilizing UD, UP, and AT individually indicated those to be the active ingredient when mixed in water and applied to mounds. Using surfactant alone, water alone, or the two in combination showed no effective kill.
9. The results clearly indicate the UD, UP, and AT individually combined with a surfactant and added to water offer superior performance over and above the commercial products tested. The UP solution is far and away the most effective of all combinations and clearly out performs by leagues other off-the-shelf products.
10. The composition of the products, or abreviations for products, embraced within this invention, that are given in Table 1 are as follows:
Product Five (P5) - ⅛ cup of Real-Pine; ⅛ cup of Dawn mixed in one gallon of water. (See Page 4 of Table 1 for composition of Real-Pine and Dawn).
Unipine 85 (UP) - A pine oil manufactured by Union Camp Corporation - 87.8% terpene alcohols; 11.9% terpene hydrocarbons; 0.3% moisture. This combination meets U.S. Government specification LLL-P-400A Type 1.
Unitene DTR (UD) - 5% terpene alcohols; 55% monocyclic hydrocarbons; 25% pine oils; 9% camphene; 6% alpha pinene; and 0.01% moisture.
Pine Oil - crude and refined. (See Table 3 for composition ranges of domestic pine oil).
Alpha Terpinol (AT).
Alpha Pinene (AP).
11. The test results indicated on Table 1 Page 3 were to test various ingredients separately from each other as well as an additional compound utilizing a mixture of ordinary peanut butter and Unipine 85 as indicated by the "product" code P5/PB/UP. In summary, the use of water as the only treatment, the use of the surfactant as the only treatment, and the use of water and surfactant in combination all had negligible results and simply caused the mound to wash away and the ants built another village. However, with the addition of Unipine 85 to water and surfactant, the combination once again proved to be very lethal.
Utilizing a similar technique, peanut butter by itself was applied to mounds with no effect. However, the addition of enough Unipine 85 to form a fairly liquid paste again caused a substantial kill. However, like Amdro, the solid bait must be ingested and it is very difficult to determine the effectiveness other than observing the dead ants on the mound surface.
It should be noted that the label on Amdro indicates this is a food chain killer wherein soldier ants carry the bait into the mound (inferring to the queen). It also indicates that it should take from one to four weeks to kill an appreciable number of soldiers and the queen. Further, the label indicates a visible reduction in mound activity should be observed in two to eight weeks. Accordingly, the mixture of peanut butter and Unipine 85 does kill in a faster time frame, at least on the surface, whereas Amdro will not kill as fast or as effectively as products of this invention. Further, when it rains, or the bait is moisturized, Amdro looses its effectiveness entirely.

TABLE 2
COMMERCIAL PRODUCTS WITH HIGHEST CONSUMER ACCEPTABILITY PROFILE

| | | |
|---|---|---|
| Product: | Raid Fire Ant Killer | |
| Manufacturer: | Johnson & Johnson | |
| Active Ing: | Chlorpyrifos [0,0-Diethyl-0-(3,5,6-trichlor-2-pyridyl)phosphorothioate | 2.00% |
| Inert Ingredients: | | 98.00% |
| EPA Reg No. 4822-264 | | |
| EPA Est No. 4822-WI-1 | | |
| Form: | Liquid | |
| Product: | Enforcer Fire Ant Killer | |
| Manufacturer: | C & J Chemical | |
| Active Ing: | Tetramethrin [1-Cyclohexene-1, 2-Dicarboximido) methyl 2, 2-Dimethyl-3-(2-methylpropenyl) Cylopropanecarboxlate] | 0.200% |
| | Cyano (3-Phenoxyphenyl) Methyl 4 chloro-alpha-(1-methylethyl) Benezeneacetate | 0.400% |
| | Petroleum Distillate | 2.278% |
| Inert Ingredients: | | 97.122% |
| EPA Reg No. 40849-13 | | |
| EPA Est No. 10807-GA-1 | | |
| 49830-GA-1 | | |
| Form: | Aerosol | |
| Product: | Rid-A-Bug | |
| Manufacturer: | Kenco Chemical & Manufacturing Company | |
| Active Ing: | Chlorpyrifos [(0.0-diethyl 0-(3,5,6-trichloro- | 0.50% |

TABLE 2-continued

COMMERCIAL PRODUCTS WITH HIGHEST CONSUMER ACCEPTABILITY PROFILE

| | | |
|---|---|---|
| | 2-pyridyl) phosphorothioate | |
| | 3,7-Dimethyl-6-octen-1-ol | 0.011% |
| | 3,7-Dimethyl-2-6-octedien-1-ol | 0.002% |
| | 3,7-Dimethyl-6-octanol | 0.002% |
| | Xylene lange aromatic solvent | 0.28% |
| Inert Ingredients: | | 99.205% |
| EPA Reg No. 8845-34 | | |
| EPA Est No. 8845-FL-1 | | |
| Form: | Liquid | |
| Product: | Amdro Fire Ant Insecticide | |
| Manufacturer: | American Cyanamid Company | |
| Active Ing: | Tetahydro-5, 5-dimethyl-2 (1 H)-phrinidinone (3-4[trifluoromethyl)phenyl]-1-(2-[4-(trifluoromethyl) phenyl]-ethenyl)-2-propenylidene | 0.88% |
| Inert Ingredients: | | 99.12% |
| EPA Reg No. 241-160 | | |
| EPA Est No. 33596-IL-01 | | |
| Form: | Granule | |

TABLE 3

COMPOSITION RANGES FOR INDIVIDUAL COMPONENTS FOUND IN DOMESTIC PINE OILS

| | RANGE FOR ALL GRADES OF PINE OIL | |
|---|---|---|
| | % Min. | % Max. |
| BI & TRICYCLIC TERPENE HYDROCARBONS | | |
| Tricyclene | ND | 0.1 |
| Alpha-Pinene | ND | 2.0 |
| Camphene | ND | 1.0 |
| Beta-Pinene | ND | 0.3 |
| MONOCYCLIC TERPENE HYDROCARBONS | | |
| cis-p-Menthane | ND | T |
| trans-p-Menthane | ND | 1.1 |
| 3-p-Menthene | ND | 0.3 |
| 1-p-Menthene (Carvomenthene) | ND | 1.2 |
| 8-Menthene | ND | 0.1 |
| 4(8)-p-Menthene | ND | T |
| alpha-Phellandrene | ND | 0.6 |
| beta-Phellandrene | ND | 0.4 |
| alpha-Terpinene | T | 2.3 |
| gamma-Terpinene | ND | 3.1 |
| Dipentene (d,l-Limonene) | 0.1 | 10.0 |
| p-Cymene | 0.1 | 4.5 |
| Terpinolene | 0.8 | 14.6 |
| 2,4(8)-p-Menthadiene | ND | 1.7 |
| alpha-p-Dimethyl-styrene | ND | 0.5 |
| TERPENE ALCOHOLS | | |
| Dihydroterpineol | ND | 6.1 |
| Terpinene-1-ol (3-p-Menthen-1-ol) | T | 13.1 |
| alpha-Fenchol | 1.5 | 11.3 |
| Terpinene-4-ol (1-p-Menthen-4-ol) | 1.1 | 11.3 |
| beta-Terpineol (cis & trans) | 0.5 | 9.2 |
| Terpineol (alpha & gamma) | 34.9 | 76.7 |
| Isoborneol | 0.1 | 4.3 |
| 1-Borneol | ND | 14.6 |
| 8-Cymenol | ND | 0.9 |
| pino-Carveol | ND | 0.4 |
| 1,8-Terpin (Terpin hydrate) | ND | 0.7 |
| MISCELLANEOUS TERPENES (Ethers & Ketones) | | |
| 1,4-Cineole | ND | 5.2 |
| 1,8-Cineole | ND | 4.2 |
| Fenchone | ND | 2.0 |
| Camphor | 0.4 | 8.3 |
| Estragole (Methyl Chavicol) | ND | 2.4 |
| cis-Anethole | ND | 6.2 |
| trans-Anethole | ND | 2.5 |
| Pinol | ND | 0.1 |
| UNKNOWNS | <0.1 | 0.4 |

ND - Not Detected
T - Trace

TABLE 4 - A

Bait Physical Characteristics

| Pine Oil % by weight | Bait* | Consistency | Odor Pine oil | Odor Bait |
|---|---|---|---|---|
| 0.1 | PB | normal for PB | none | strong |
| 0.5 | PB | normal for PB | faint | strong |
| 1.0 | PB | normal for PB | distinct | strong |
| 1.0 | DF | dry grains | faint | faint |
| ~1 | BR | fine granules | | |
| 5.0 | PB | paste | distinct | strong |
| 5.0 | DF | dry grains | weak | weak |
| 10.0 | PB | paste | distinct | faint |
| 10.0 | DF | dry grains | distinct | weak |
| 10.0 | BR | granules | | |
| 15.0 | PB | runny paste | distinct | faint |
| 15.0 | DF | sticky grains | distinct | distinct |
| 20.0 | PB | runny paste | distinct | faint |
| 20.0 | DF | sticky grains | distinct | distinct |
| 25.0 | PB | thick liquid | distinct | faint |
| 25.0 | DF | sticky grains | distinct | distinct |
| 25 | BR | coarse grounds | | |
| 30.0 | PB | thick liquid | distinct | faint |
| 30.0 | DF | sticky grains | strong | distinct |
| 35.0 | DF | wet grains | strong | weak |
| 40.0 | DF | wet grains | strong | weak |
| 45.0 | DF | liquid + grains | strong | none |
| 50.0 | DF | liquid + grains | strong | none |
| 50 | BR | small chunks | | |
| 75 | BR | chunks | | |

TABLE 4 - B

100% Kill Times Ventilated Jars

| Pine Oil by Weight | Bait* | Time |
|---|---|---|
| ~1 | BR | 36 hours** |
| 1.0 | DF | <12 hours |
| 5.0 | DF | <12 hours |
| 10 | BR | 45 minutes |
| 10.0 | DF | <3 hours |

TABLE 4 - B-continued

| 100% Kill Times Ventilated Jars | | |
|---|---|---|
| Pine Oil by Weight | Bait* | Time |
| 15.0 | DF | <3 hours |
| 25 | BR | 30 minutes |
| 25.0 | DF | <3 hours |
| 30.0 | DF | <1 hour |
| 40.0 | DF | <1 hour |
| 50 | BR | 20 minutes |
| 75 | BR | 10 minutes |

*PB Peanut Butter
DF Dry Dog Food
BR Bread
**mixture not completely homogeneous - some ants died much more quickly Among the active ingredients for killing or controlling fire ants that may be employed in accordance with my invention are specific components of pine oil. For example, I have found that alpha-pinene per se may be used instead of the pine oil in the same manner as above described with enhanced results. Also, the specific fractions of pine oil resulting from its distillation are effective fire ant killers. For example, I have found that although crude pine oil is effective, refined pine oil which has a larger conncentration of alpha-pinene is more effective. Alternatively, synthetic pine oil may be substituted in whole or in part for the natural material.

In accordance with this invention, instead of employing just pine oil with the bait, one may employ the compositions of my copending application Ser. No. 17,739 which include a surfactant and water, and which may include an alcohol to facilitate the formation of the paste form.

Various alcohols may be employed in place of the methyl alcohol used in the preferred embodiment of my invention. The lower aliphatic alcohols such as ethyl, propyl, butyl and similar alcohols may be used in whole or in part with the preferred methyl alcohol of this invention.

The surfactants that may be used are those which cause the emulsification of the pine oil/alcohol mixture of this invention. For example ordinary soap may be used or even the household detergents used for laundry or dishes may be used. The preferred surfactants to employed in accordance with my invention are products having a composition or function similar to Dawn. The amount of surfactant used to make the emulsions of the pine oil water mixture is only that amount necessary to make the emulsions. For example, when using concentrations of pine oil at the lower end of the preferred range in one gallon of water smaller amounts of liquid surfactant may be employed than when using concentrations of pine oil at the higher end of the preferred range.

The baits which may be employed include alfalfa meal, beef fat, blood meal, bacon, beef bouillon, corn meal, casein, corn, ground corn cobs, cotton seed meal, chicken feed, dog food, dried apple, egg, fish meal, flour, honey, meat, oats, peanuts, peanut butter, peanut meal, raisins, sausage, sawdust, sugar, soybean meal, tankage, wheat, oats, bran, whey, cattle feed, bread, crackers, St. Johns bread, chocolate, dog biscuits, packing house wastes, grain, seeds, butter, bacon drippings, corn oil, soft drink syrup, cotton seed oil, lard, chocolate syrup, molasses, sugar syrup, peanut oil, vegetable oil, corn protein hydrolysate, soups and bouillons, mayonnaise, milk, cream and aromatic natural oils. Other baits may be employed in solid, paste, liquid, gaseous, or mist form including mixtures or suspensions thereof, to make the insecticidal compositions of this invention. The controlling factor in selecting the bait is that the fire ants are not repelled by it but rather like it when in combination with the pine oil active ingredient of this invention.

The formulations may also contain odorants which are attractive to fire ants. These in combination with the pine oil enhance the respiratory kill effect on the fire ants. They may also contain pigments to serve to distinguish the compositions from human or animal food substances. They may also contain odorants which are repulsive to humans and animals to prevent the compositions form being consumed by them. They may also be formulated to prevent spoilage by including anti-oxidants, bacteriostats, fungistats, and so forth.

The concentrations of ingredients in the compositions of this invention may be varied. For example, although proportions of between about 1 part of pine oil to about 99 parts of bait and about 99 of pine oil to about 1 of bait is preferred because of economic practicality, more or less of each may be used and all that is required is an insecticidal amount of pine oil and an amount of bait that is attractive to the fire ants. However, when more pine oil is used in the formulation, there is faster and more effective kill of the fire ants. By increasing the strength of the pine oil active ingredient, one can expect to decrease the kill time. Accordingly it is only necessary to use an effective insecticidal amount of pine oil active ingredient for the type and kind of result desired.

The formulations of this invention may be prepared by mixing the ingredients to be included in the final formulation in conventional manner. For example by blending, kneading, homoginizing and in some cases such as making small concentrations of pine oil in peanut butter, melting the bait and then blending in the pine oil to get more uniform distribution of the active ingredient in the bait. Also suspensions, such as colloidal suspensions or mixtures of the pine oil active ingredient with liquid baits may be used. Solid baits such as dry dog food may be sprayed, soaked or drenched with the pine oil active ingredient depending on the amounts of each employed. The solid forms may be made into dusting formulations using carriers such as talc or finely divided clays and the like, with or without additives as discussed above. Also surface active carriers, such as activated carbon which adsorb the pine oil active ingredient of this invention may be employed. The gaseous or mist forms are also prepared in conventional manner, including preparation with propellants, such as the freons and other gaseous propellants, with and without the additives discussed above.

It is to be understood that various modifications within the spirit and scope of my invention are possible, some of which have been referred to above, and although I have given detailed description of my invention by illustrating specific embodiments, I do not intend to be limited thereto, except as defined by the following claims.

I claim:

1. A composition for controlling fire ants consisting of a mixture of an insecticidal amount of pine oil surfactant and bait in solid or fluid form.

2. A composition in accordance with claim 1 wherein the pine oil and bait are present in proportions of between about 1 part of pine oil to about 99 parts of bait and about 99 of pine oil to about 1 of bait.

3. A composition in accordance with claim 1 wherein the bait is a solid.

4. A composition in accordance with claim 1 wherein the fluid form of bait is a liquid.

5. A composition in accordance with claim 1 wherein the fluid form of bait is water.

6. A composition in accordance with claim 1 wherein the fluid form of bait is a paste.

7. A composition in accordance with claim 1 wherein the mixture of pine oil surfactant and bait, further contains a spoilage retardant.

8. A composition in accordance with claim 6 wherein the composition further contains an odorant.

9. A method for controlling fire ants which comprises applying a mixture of an insecticidal amount of pine oil and bait in solid or fluid form, to the locus containing the fire ants.

10. A method for controlling fire ants in accordance with claim 9 wherein the pine oil and bait are present in proportions of between about 1 part of pine oil to about 99 parts of bait and about 99 of pine oil to about 1 of bait.

11. A method for controlling fire ants in accordance with claim 9 wherein the bait is a solid.

12. A method for controlling fire ants in accordance with claim 9 wherein the bait is a fluid.

13. A method for controlling fire ants in accordance with claim 9 wherein the fluid form of bait is a paste.

14. A method for controlling fire ants in accordance with claim 9 wherein the fluid form of bait is a syrup.

15. A method for controlling fire ants in accordance with claim 9 wherein the fluid form of bait is a mist.

16. A method for controlling fire ants in accordance with claim 9 wherein the fluid form of bait is a gas.

17. A method for controlling fire ants in accordance with claim 9 wherein the fluid form of bait is a liquid.

18. A method for controlling fire ants in accordance with claim 9 wherein the fluid form of bait is water.

* * * * *